(12) United States Patent
Protopsaltis

(10) Patent No.: US 8,636,654 B2
(45) Date of Patent: Jan. 28, 2014

(54) RETRACTORS FACILITATING IMAGING DURING SURGERY

(75) Inventor: Dimitri Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 941 days.

(21) Appl. No.: 11/640,785

(22) Filed: Dec. 18, 2006

(65) Prior Publication Data

US 2008/0146885 A1 Jun. 19, 2008

(51) Int. Cl.
*A61B 1/32* (2006.01)

(52) U.S. Cl.
USPC .............................. 600/201; 600/208; 600/210

(58) Field of Classification Search
USPC ........................... 600/201, 224, 233, 210–219
See application file for complete search history.

(56) References Cited

U.S. PATENT DOCUMENTS

| | | | |
|---|---|---|---|
| 3,851,642 A * | 12/1974 | McDonald | 600/212 |
| 5,512,038 A | 4/1996 | O'Neal et al. | |
| 6,855,148 B2 | 2/2005 | Foley et al. | |
| 6,869,398 B2 * | 3/2005 | Obenchain et al. | 600/224 |
| 2004/0015173 A1 * | 1/2004 | Irving | 606/88 |
| 2004/0116777 A1 * | 6/2004 | Larson et al. | 600/210 |
| 2005/0065517 A1 | 3/2005 | Chin | |
| 2005/0070765 A1 * | 3/2005 | Abdelgany et al. | 600/214 |
| 2005/0080319 A1 | 4/2005 | Dinkler, II et al. | |
| 2005/0080320 A1 * | 4/2005 | Lee et al. | 600/214 |
| 2005/0085723 A1 | 4/2005 | Huebner | |
| 2005/0159651 A1 * | 7/2005 | Raymond et al. | 600/213 |
| 2006/0052672 A1 * | 3/2006 | Landry et al. | 600/233 |
| 2006/0069404 A1 | 3/2006 | Shluzas et al. | |
| 2006/0074445 A1 | 4/2006 | Gerber et al. | |
| 2006/0122462 A1 | 6/2006 | Roth et al. | |
| 2007/0027364 A1 * | 2/2007 | Schwer | 600/219 |

* cited by examiner

Primary Examiner — Ellen C Hammond
Assistant Examiner — Stuart S Bray
(74) Attorney, Agent, or Firm — Sorell Lenna & Schmidt LLP

(57) ABSTRACT

Tissue retraction devices and methods include a tissue retractor with a radiolucent portion to permit imaging through the radiolucent portion with X-ray, fluoroscopic or other suitable imaging system. The tissue retractor also includes one or more radio-opaque elements that define at least a portion of a perimeter of the radiolucent portion to provide an indication of the retractor location in the patient via the imaging system.

25 Claims, 5 Drawing Sheets

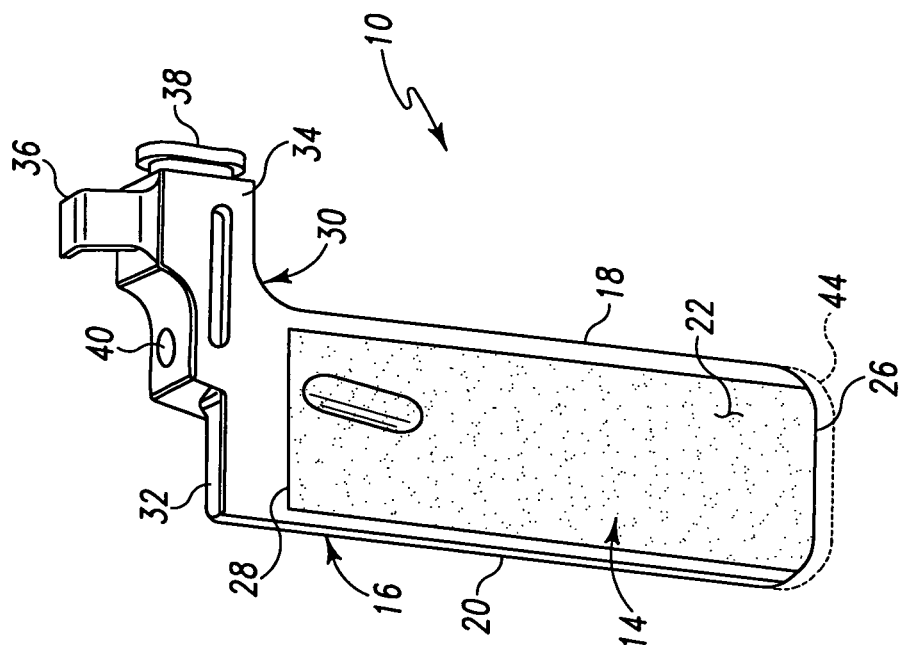
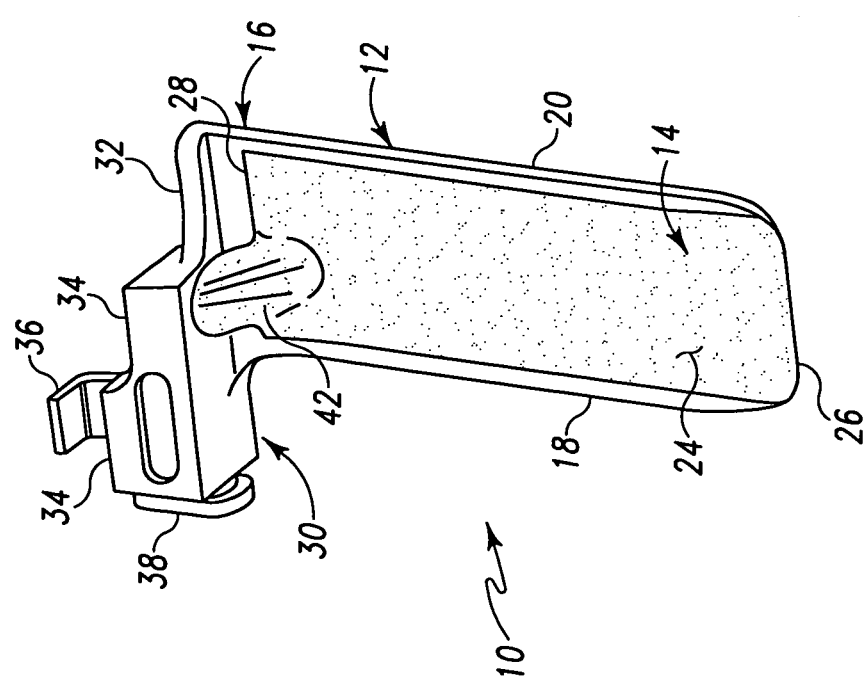

RETRACTORS FACILITATING IMAGING DURING SURGERY

BACKGROUND

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of surgical retractors and techniques that minimize the size of the incision has yielded a major improvement in reducing recovery time and post-operative pain because minimal dissection of tissue, such as muscle tissue, is required and impact on nerve tissue is minimized. For example, minimally invasive surgical techniques are desirable for spinal and neurosurgical applications because of the need for access to locations within the body and the danger of damage to vital intervening tissues. However, visualization of tissue, implants and instruments during surgery from the proximal end of the retractor or from within the retractor can be difficult, particularly when the size of the approach in the patient to the operative site is minimized, or when the procedure occurs at a location deep within the body of the patient. While developments in surgery have provided improved patient outcomes, there remains a need for further developments that facilitate the use of surgical instruments and the surgeon's ability to manipulate instruments and implants in the surgical approach and operative site during the surgery.

SUMMARY

Retractors are provided with one or more blade portions or sleeve portions that include one or more radiolucent portions and one or more radio-opaque portions.

According to one aspect, tissue retraction devices and methods include a tissue retractor with a radiolucent portion to permit imaging through the radiolucent portion with X-ray, fluoroscopic or other suitable imaging system, providing the surgeon an indication of the surgical approach and operative site in the patient from trajectories other than through the proximal end of the retractor device or from within the retractor. The tissue retractor also includes one or more radio-opaque elements that define at least a portion of a perimeter of the radiolucent portion to provide an indication to the surgeon of the retractor location and boundaries of the retractor in the patient via the imaging system.

Surgical methods include positioning at least one blade or sleeve portion of a surgical retractor in a patient and imaging the surgical approach or operative site in the patient through tissue of the patient and through a radiolucent portion of the blade or sleeve portion. The surgical methods also include locating the blade or sleeve portion in the patient by imaging a radio-opaque portion of the blade or sleeve portion through tissue of the patient.

These and other aspects will be discussed further below.

BRIEF DESCRIPTION OF THE FIGURES

FIG. 1 is a perspective view of one embodiment retractor.

FIG. 2 is a perspective view of the retractor of FIG. 1 looking toward a side of the retractor opposite the side toward which FIG. 1 is directed.

DESCRIPTION OF THE ILLUSTRATED EMBODIMENTS

Figure 3:
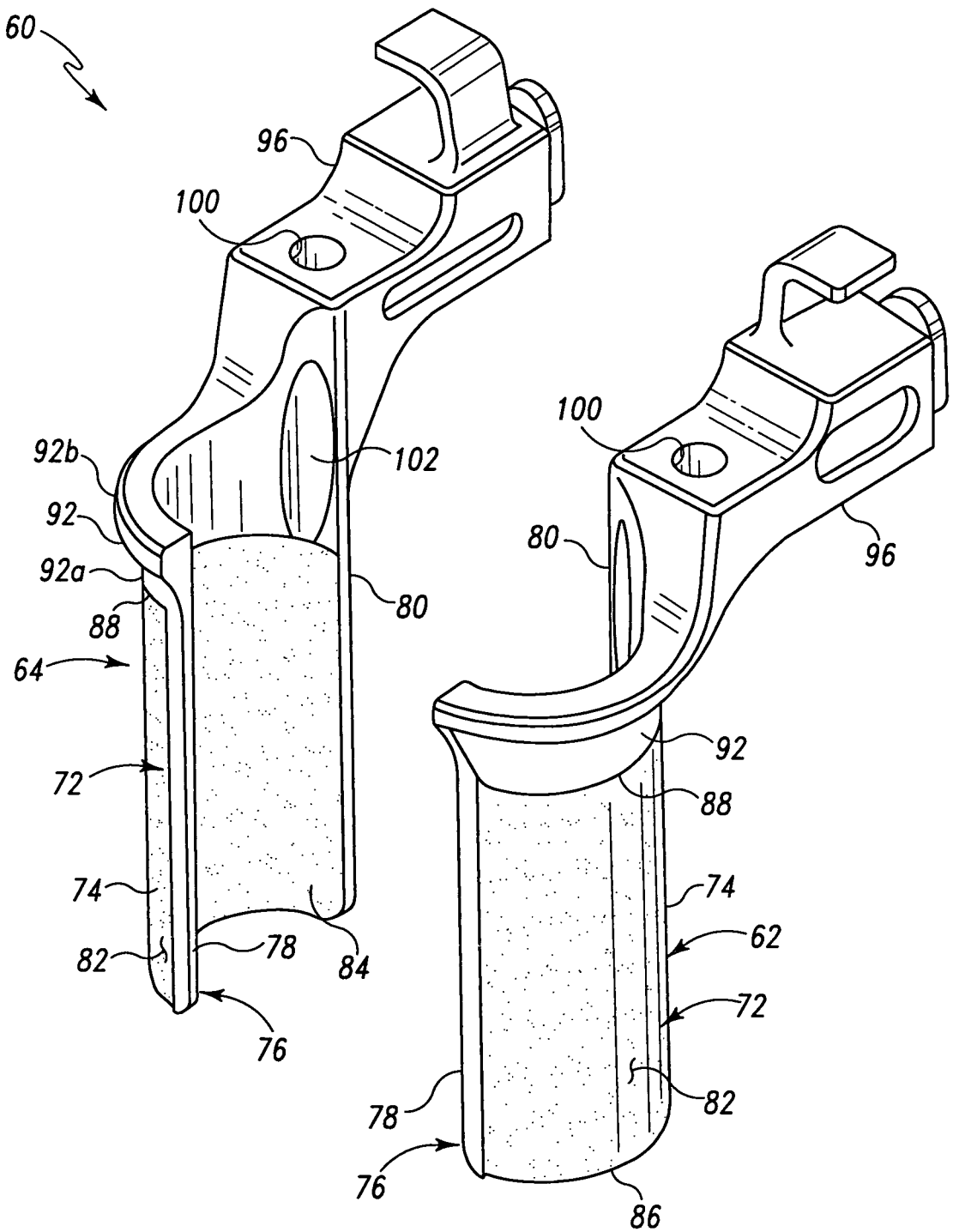
FIG. 3 is a perspective of another embodiment retractor with a pair of retractor portions spaced from one another.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

In FIGS. 1 and 2, there is shown a retractor 10. Retractor 10 is positioned into a patient during a surgical procedure to move or retain tissues along an approach to an operative site in the patient. Retractor 10 includes a blade portion 12 having a radiolucent portion 14 and a radio-opaque portion 16. Radiolucent portion 14 includes flat, planar tissue contacting surface 24 on one side thereof and an opposite flat, planar inner surface 22 opposite tissue contacting surface 24. Radiolucent portion 14 comprises the majority of the surface area of blade portion 12 to permit imaging through tissue of the patient and through blade portion 12 using radiographic, fluoroscopic, or any other suitable imaging system. Surgical instruments and implants in the surgical approach and operative site can also be imaged without substantial obstruction by radiolucent portion 14. This permits the surgeon to effectively employ the imaging system in guiding and positioning the implants and instruments along the approach defined by blade portion 12 and to the operative site located at or adjacent the distal end of blade portion 12.

Radiolucent portion 14 extends between longitudinally extending members 18 and 20 of radio-opaque portion 16. Longitudinally extending members 18, 20 are located on opposite sides of radiolucent portion 14, and define a portion of the perimeter of blade portion 12. Longitudinally extending members 18, 20 are imaged with the imaging system and provide an indication to the surgeon of the boundaries or perimeter of blade portion 12 to the surgeon along the approach to the operative site. Accordingly, the surgeon can readily locate and control the positioning of instruments and implants along the approach to the operative site so that the instruments and implants are maintained within the confines of blade portion 12 based on the boundaries of blade portion 12 indicated by the imaging of radio-opaque portion 16.

Radiolucent portion 14 can be made from any suitable radiolucent material, such as carbon fiber, polyetheretherketone, plastics, or polymer materials, for example. Radio-opaque portion 16 can be comprised of any biocompatible radio-opaque material. Examples include metals and metal alloys such as stainless steel.

Radio-opaque portion 16 includes longitudinally extending members 18, 20 that are in the form of elongated bars or channels that frame the sides of radiolucent portion 14. Longitudinally extending members 18, 20 extend from distal edge 26 of radiolucent portion 14 proximally to a proximal transverse member 32. Longitudinally extending members 18, 20 are secured to radiolucent portion with any one or combination of adhesives, friction fit, fasteners, over-molding, interlocking components, or other suitable fastening technique or system. Radio-opaque portion 16 also includes, in an alternate embodiment, a distal transverse member 44 that extends between members 18, 20 along the distal edge 26 of blade portion 12, as indicated in dashed lines in FIG. 2.

Radio-opaque portion 16 includes a proximal connecting structure 30 located at the proximal end 28 of blade portion 12. Connecting structure 30 includes proximal transverse member 32 extending along the proximal edge 28 of radiolucent portion 14 and a connecting arm 34 extending laterally outwardly from transverse member 32. Transverse member 32 includes a distal portion that forms a proximal extension of the blade portion 12, and also includes a proximal portion that forms a lip extending outwardly for mounting of instruments or the like. Connecting arm 34 includes an end connector 38 forming a recessed groove and an end member for attachment to a support structure (not shown) or a separation instrument (discussed below.) Connecting arm 34 includes an increased width and thickness relative to transverse member 32 and forms a platform for engagement to the support structure or separation instrument and to transmit retraction loads from blade portion 12 to the support structure without bending or flexing.

Blade portion 12 is offset along one side of connecting arm 34 so that when retractor 10 is employed with a second retractor the inner surfaces 22 face one another. The planar adjacent inner surfaces can be positioned in contact or nearly in contact with one another to minimize the space therebetween. After positioning in the incision, the retractor portions can be moved away from one another to define a working channel therebetween and an approach to the operative site. Various separation instruments are contemplated that can be engaged to the retractor portions to move the retractor portions toward and away from one another, examples of which are provided in U.S. patent application Publication No. 2005-0234304 published on Oct. 20, 2005, which is incorporated herein by reference.

Connecting structure 30 also defines a portion of passage 40 that opens in a proximally oriented surface of connecting arm 34 and extends therefrom to an opposite opening in inner surface 22 of blade portion 12. Passage 40 can receive an illumination instrument, suction instrument, irrigation instrument, or other surgical instrument therethrough so that the surgical instrument is positioned along the inner surface 22 for use at the operative site or in the approach to the operative site. Connecting arm 34 includes a retaining member 36 forming a hook shape extending proximally from connecting arm 34 that can receive the instrument from passage 40 and contour or hold it away from the approach to the operative site define by the proximal end of retractor 10. As shown in FIG. 1, radiolucent portion 14 includes a tubular protruding portion 42 extending from tissue contacting surface 24 to connecting arm 34 to provide passage 40 with an enclosed configuration along the length of passage 40.

Figure 4:
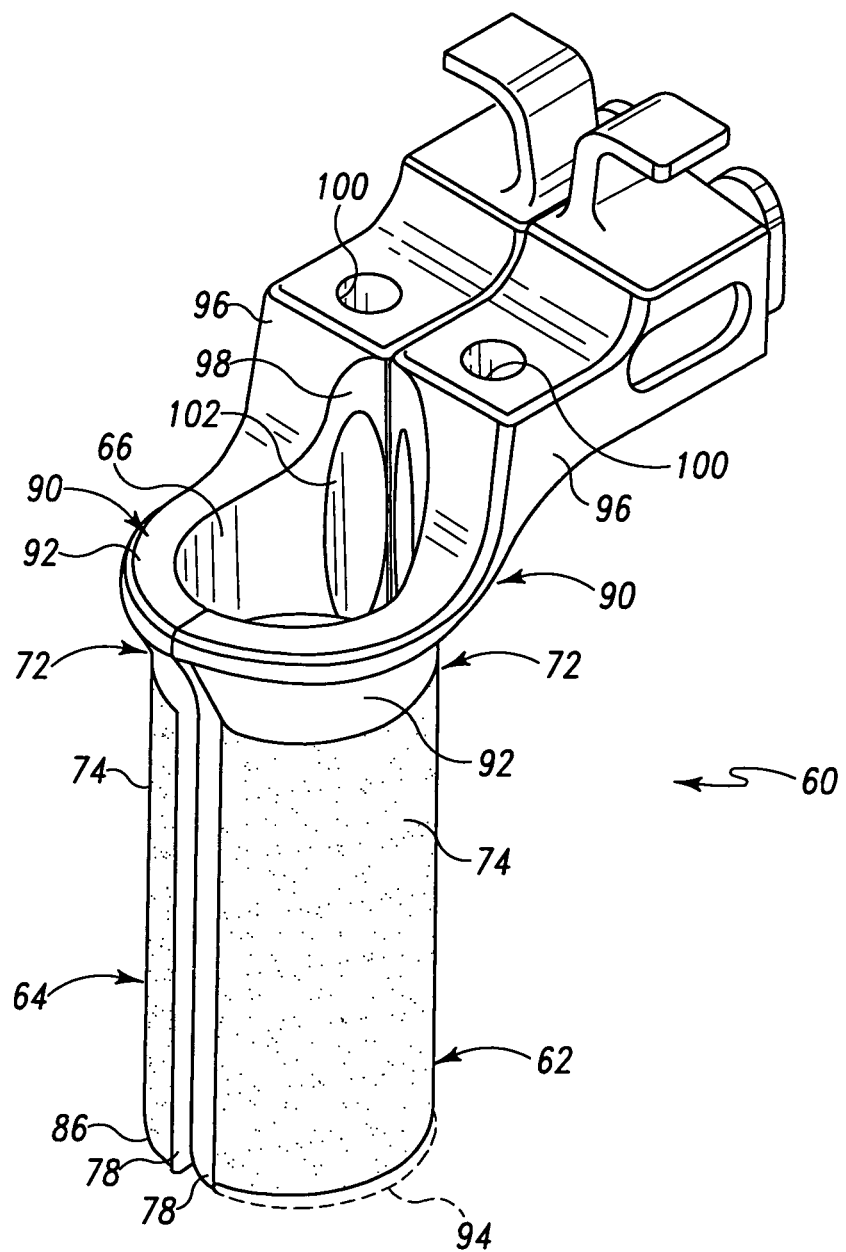
FIG. 4 is a perspective view of the retractor of FIG. 3 with the retractor portions positioned adjacent one another.

In FIGS. 3 and 4, there is shown a retractor 60 that includes first and second retractor portions 62, 64. Retractor portions 62, 64 are mirror images of one another, and will be described together below using the same reference numerals for like elements. First and second retractor portions 62, 64 are connectable to and movable toward and away from one another with a separation instrument, such as described in U.S. patent application Publication No. 2005/0234304. In FIG. 4, retractor portions 62, 64 are positioned adjacent one another to define and completely enclose a working channel 66 in a closed configuration. Radiolucent portion 74 includes convexly curved outer tissue contacting surface 82 on one side thereof and a concavely curved inner surface 84 opposite tissue contacting surface 82 that extends along working channel 66. In the closed configuration, insertion of retractor 60 into the incision is facilitated since its lateral dimension is minimized. In one procedure, retractor 60 is positioned in the closed configuration over a dilator or directly into the incision in the reduced size configuration. In order to enlarge the working channel and to increase the size of the surgical approach and provide greater access to the operative site by displacing the tissue of the patient, retractor portions 62, 64 are laterally separated from one another, such as shown in FIG. 3.

It is also contemplated that retractor portions 62, 64 can be pivoted so that their distal ends move away from one another to increase the size of the surgical approach. In other embodiments, lateral separation and pivoting of the retractor portions provides a surgical approach that is greater in size than the initial insertion configuration. In still other embodiments, only one retractor portion 62, 64 is provided to form a surgical approach to the operative site. In yet another embodiment, retractor portions 62, 64 are not identical. For example, one retractor portion can be configured that is entirely radio-opaque, or that is configured like retractor 10 discussed above, or with some other configuration.

Retractor portions 62, 64 each include a blade portion 72 having a radiolucent portion 74 and a radio-opaque portion 76. Radiolucent portion 74 comprises the majority of the surface area of blade portion 72 to permit imaging through blade portion 72 using a radiographic, fluoroscopic, or any other suitable imaging system. Surgical instruments and implants can be imaged in the working channel without substantial obstruction by radiolucent portion 74, permitting the surgeon to effectively employ the imaging system in guiding and positioning the implants and instruments along the approach and operative site defined by retractor 60 by providing images of the location and orientation of the same from an approach that is remote from the working channel or the proximal end of the retractor 60.

Radiolucent portion 74 extends between longitudinally extending members 78 and 80 of radio-opaque portion 76. Longitudinally extending members 78, 80 are located on opposite sides of radiolucent portion 74, and define a portion of the perimeter of blade portion 72. Longitudinally extending members 78, 80 are imaged with the imaging system and provide an indication to the surgeon of the extent and location of the boundaries or perimeter of blade portion 72 to the surgeon along the approach to the operative site. Accordingly, the location of instruments and implants positioned through the approach to the operative site can be controlled and maintained within the confines of retractor 60 based on the location of the boundaries of blade portions 72 indicated by the imaging system.

Radiolucent portion 74 can be made from any suitable biocompatible radiolucent material, such as carbon fiber, polyetheretherketone, plastics, or polymer materials, for example. Radio-opaque portion 76 can be comprised of any biocompatible radio-opaque material. Examples include metals and metal alloys such as stainless steel.

Radio-opaque portion 76 includes longitudinally extending members 78, 80 that are in the form of elongated bars that frame the sides of radiolucent portion 74. Longitudinally extending members 78, 80 extend from distal edge 86 of radiolucent portion 74 proximally to a proximal transverse member 92. Longitudinally extending members 78, 80 are secured to radiolucent portion with any one or combination of adhesives, friction fit, fasteners, over-molding, interlocking components, or other suitable fastening technique or system. Radio-opaque portion 76 also includes, in an alternate embodiment, a distal transverse member 94 that extends between longitudinally extending members 78, 80 along the distal edge 86 of blade portion 72, as indicated in dashed lines in FIG. 4.

Radio-opaque portion 76 includes a proximal connecting structure 90 located at the proximal end 88 of blade portion 72. Connecting structure 90 includes transverse member 92 extending along the proximal edge 88 of radiolucent portion 74 and a connecting arm 96 extending from transverse member 92. Connecting arms 96 are positioned adjacent one another in the closed configuration shown in FIG. 4, and the arcuate blade portions 72 extend around and enclose working channel 66. Transverse member 92 includes a distal portion 92a that forms a proximal extension of the respective blade portion 72, and includes a proximal portion 92b that forms a lip extending radially outwardly for mounting of instruments or the like. Connecting arm 96 is configured like connecting arm 34 discussed above except for passage 100. Passage 100 is like passage 40 in that it is provided for receiving surgical instruments and opens in the proximal side of connecting arm 96. However, passage 100 extends from its proximal opening to a distal opening 102 along an inner surface 98 of connecting arm 96 adjacent working channel 66.

In the closed configuration, longitudinally extending members 78 of the respective retractor portions 62, 64 are positioned in side-by-side relation to one another. Likewise, the longitudinally extending members 80 of the respective retractor portions 62, 64 are positioned in side-by-side relation. The adjacent longitudinally extending member 78, 80 can contact one another to limit movement of the retractor portions 62, 64 toward one another. Radiolucent portions 74 permit imaging with the imaging system of surgical instruments and implants in working channel 66 and at the operative site distal of retractor 60 through tissue of the patient and through the radiolucent portions 74. The relative positioning of retractor portions 62, 64 in relation to one another and to the patient can be determined in situ by radiographic or fluoroscopic imaging through the tissue of the patient the radio-opaque longitudinally extending members 78, 80. Instruments and implants can be maintained and controlled within the confines and boundaries of the retractor portions 62, 64 to prevent encroachment into the tissue adjacent to retractor portions 62, 64.

Figure 5:
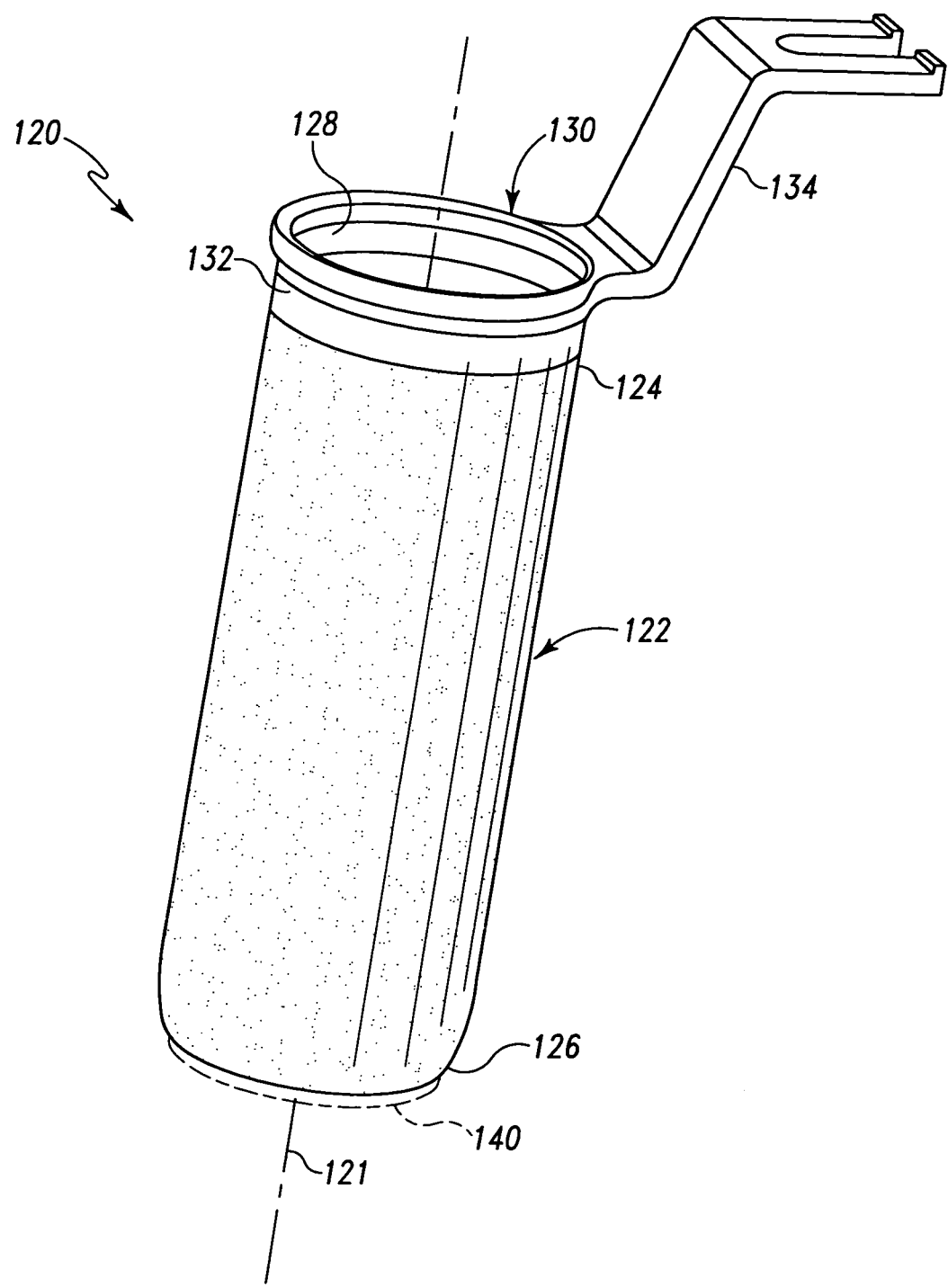
FIG. 5 is a perspective view of another embodiment retractor.

FIG. 5 shows another embodiment retractor 120 that includes a radiolucent sleeve portion 122 extending between a proximal end 124 and a distal end 126. Sleeve portion 122 is elongated and includes a circular cross-section orthogonally to longitudinal axis 121. Sleeve portion 122 defines a working channel 128 extending between and opening at proximal and distal ends 124, 126. Retractor 120 also includes a radio-opaque portion 130 extending about the proximal end of sleeve portion 122 that provides an indication of the location of retractor 120 relative to the patient and to surgical instruments and implants in sleeve 122 when retractor 120 is imaged with a radiographic or fluoroscopic imaging system. Radio-opaque portion 130 includes a ring member 132 extending around sleeve portion 122. Ring member 132 includes a distal portion that forms an extension of sleeve portion 122, and a proximal portion that forms a radially outwardly extending lip for mounting of instruments or the like. Radio-opaque portion 130 also includes an optional bracket member 134 extending from ring member 132 that can be secured to a flexible arm or other device associated with the surgical table to hold retractor 120 in position.

Retractor 120 also includes, in another embodiment, a distal radio-opaque portion 140 at the distal end of sleeve portion 122, as indicated by dashed lines in FIG. 5. Distal portion 140 forms a ring extending around working channel 128 and provides an indication of the location of distal end 126 in the patient when imaged with the imaging system. The radiolucent sleeve portion 122 permits radiographic or fluoroscopic imaging of surgical instruments and implants in working channel 128 and at the surgical site at the distal end of retractor 120 through the tissue of the patient and without substantial obstruction from sleeve portion 122.

The retractors herein define enclosed or substantially enclosed working channels or approaches to the surgical site at the distal end of the retractor in some embodiments. The enclosed working channels define circular, oval, rectangular or other cross-sectional shape orthogonally to the longitudinal axis. Some embodiments of the retractors have retractor portions that are movable away from one another by translation and/or by pivoting the retractor portions to enlarge the working channel or surgical approach. In the enlarged configuration, the surgical approach can have a cylindrical or frusto-conical shape with, for example a cross-section that is oval, elliptical, circular, curved, polygonal, or combined polygonal/curved in shape. Still other embodiments utilize a single retractor portion so that one side of the approach is defined by the tissue of the patient opposite the blade portion of the retractor.

Figure 6:
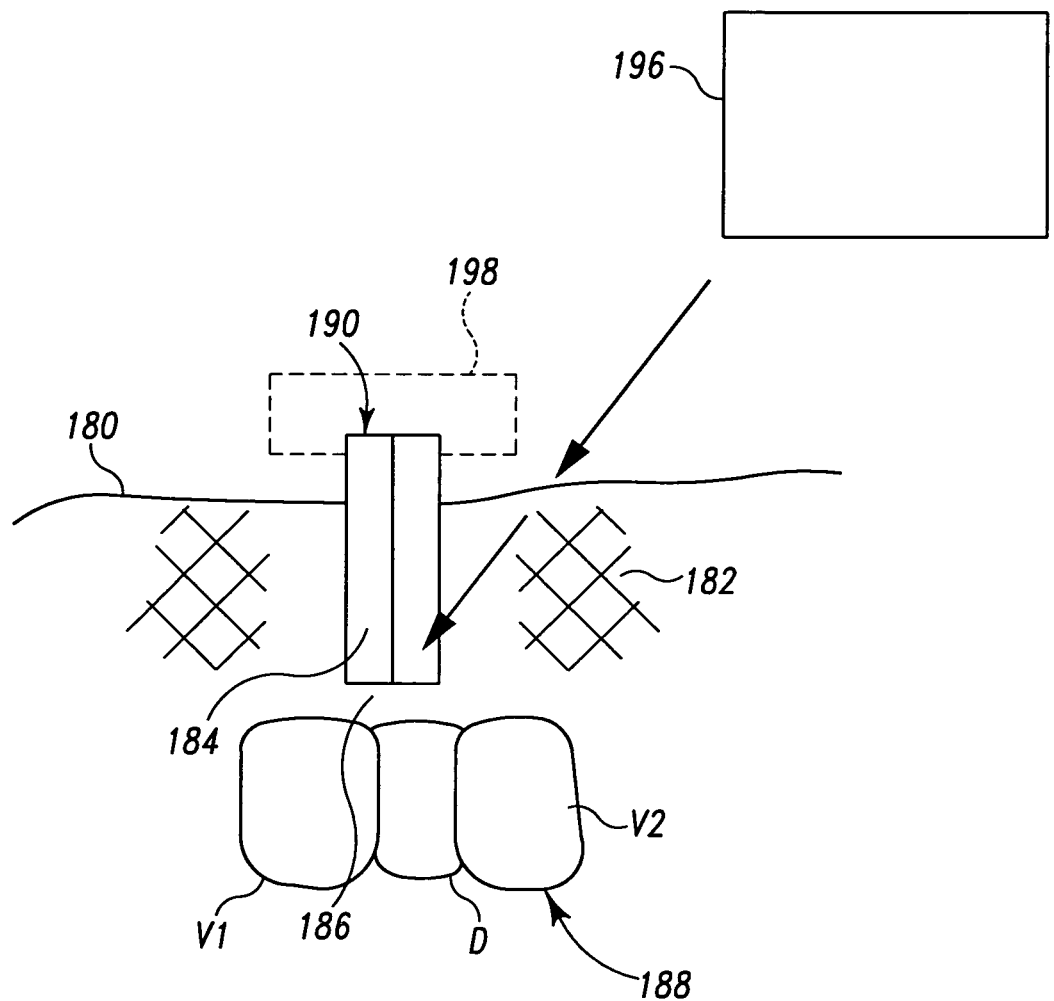
FIG. 6 is a diagram showing a surgical approach to a surgical site with a retraction device and imaging system.

Referring now to FIG. 6, one example of a method for imaging the surgical approach and surgical site in the patient through the retractors herein will be described. Retraction device 190 is any of the retractor embodiments discussed herein. An incision is made in skin 180 adjacent the location of a patient's anatomy to be accessed. For example, in spinal surgery, the incision can be made at a vertebral level 188 at a location that provides access to the disc space D between adjacent vertebrae V1, V2, or to the bony structure of one or more vertebrae V1, V2 through a desired surgical approach 184. Examples of suitable approaches include posterior, postero-lateral, lateral, antero-lateral, and anterior approaches to the spinal column. Prior to insertion of retraction device 190, which can be any of the retractor embodiments discussed herein, skin 180 and tissue 182 can be sequentially dilated via dilation instruments (not shown) which can include guidewires and/or one or more tissue dilators of increasing size. Other procedures contemplate that the tissue is not dilated, but rather the retraction device 190 is inserted in the incision and manipulated to provide surgical approach 184 to the operative site 186 at the distal end of retraction device 190. For certain embodiments, separation instrument 198 is manipulated to separate the retractor portions by translation and/or pivoting to increase the size of surgical approach 184.

An imaging system 196, such as a fluoroscopic, radiographic, CT scan, or other imaging system, can be used to provide images to the surgeon of the surgical approach 184 and operative site 186 through the tissue of the patient and through the radiolucent portion of retraction device 190. The radio-opaque portion of retraction device 190 provides an indication of the outer perimeter and boundaries of at least a portion of retraction device 190 along the surgical approach 184 and relative to the operative site 186. Thus, the surgeon is assisted in maintaining surgical instruments and implants within surgical approach 184. Furthermore, the location and orientation of the instruments and implants at operative site 186 can be determined with imaging system 196 through the radiolucent portion of retraction device 190 and the tissue of the patient. For embodiments of retraction device 190 with a distal transverse radiolucent member, the location of the distal end of retraction device 190 relative to the operative site, and the relative positioning of the implants and instruments in or adjacent the retraction device 190, can also be determined with imaging system 196 through the tissue and the radiolucent portions of the retraction device 190.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A tissue retraction device for surgery in a patient, comprising:
   a retractor comprising an elongated blade portion extending between a proximal end and a distal end, wherein said distal end is positionable in the patient, said blade portion including a radiolucent portion extending between said distal and proximal ends and between opposite sides of said blade portion, said blade portion further including a radio-opaque longitudinal member extending on at least one of said opposite sides thereof in a direction between said distal and proximal ends to define at least a portion of an outer perimeter edge of said blade portion and provide an indication of a location and extent of said blade portion in the patient, said blade portion further including a passage configured for receiving a surgical instrument, said passage extending between a first opening extending through the proximal end and a second opening extending through one of said opposite sides, said first opening being positioned equidistant between said opposite sides.

2. The device of claim 1, wherein said radio-opaque longitudinal member includes first and second radio-opaque longitudinal members extending on a respective one of said opposite sides to define opposite outer perimeter edges of said blade portion.

3. The device of claim 2, further comprising a radio-opaque end member extending from said first radio-opaque longitudinal member to said second radio-opaque longitudinal member on a distal edge of said blade portion.

4. The device of claim 3, further comprising a proximal connecting member extending along said proximal end of said blade portion, said connecting member being comprised of radio-opaque material.

5. The device of claim 2, wherein:
   said blade portion includes a first side surface and an opposite second side surface, said first and second side surfaces extending between said opposite sides and between said distal and proximal ends; and
   said first and second side surfaces are each planar.

6. The device of claim 5, further comprising a passage opening in said first side surface and extending from said proximal end first through a proximal connecting structure at said proximal end of said blade portion.

7. The device of claim 2, wherein:
   said blade portion includes a first side surface and an opposite second side surface, said first and second side surfaces extending between said opposite sides and between said distal and proximal ends; and
   said opposite edges each extend to said opposite first and second side surfaces.

8. The device of claim 2, wherein said first and second radio-opaque longitudinal members are elongated bar-like members that extend along an entire length of said respective side from said proximal end to said distal end of said blade portion.

9. The device of claim 1, wherein said radiolucent portion is comprised of a polymer material and said radio-opaque longitudinal member is comprised of metal material.

10. The device of claim 1, wherein the first opening is circular.

11. The device of claim 1, wherein the second opening is oval.

12. The device of claim 1, wherein the first opening has a circular cross section.

13. The device of claim 1, wherein the second opening does not extend through the radiolucent portion.

14. The device of claim 1, wherein the blade portion defines a longitudinal axis, the proximal end includes a connecting structure extending perpendicular to the longitudinal axis, and the first opening extends through the connecting structure.

15. The device of claim 1, further comprising a surgical instrument positioned within the passage such that the surgical instrument engages one of said opposite sides.

16. The device of claim 1, wherein the proximal end is free of any protrusions.

17. The device of claim 1, wherein the first opening has a maximum width that is less than a maximum width of the second opening.

18. A tissue retraction device for surgery in a patient, comprising:
   a retractor comprising an elongated blade portion extending between a proximal end and a distal end, wherein said distal end is positionable in the patient, said blade portion including a radiolucent portion extending between said distal and proximal ends and between opposite sides of said blade portion, said blade portion further including first and second radio-opaque longitudinal members extending on opposite sides of said radiolucent portion between said distal and proximal ends of said blade portion to define an outer perimeter edge of said blade portion with said first and second radio-opaque longitudinal members extending to oppositely facing first and second side surfaces of said blade portion and said first and second radio-opaque longitudinal members provide an indication of a location and extent of said blade portion in the patient, said blade portion further including a passage configured for receiving a surgical instrument, said passage extending between a first opening extending through the proximal end and a second opening extending through one of said opposite sides, said first opening being positioned equidistant between said opposite sides.

19. The device of claim 18, further comprising a radio-opaque end member extending from said first longitudinal member to said second longitudinal member along said distal end of said blade portion.

20. The device claim 18, wherein said first and second side surfaces extend between said opposite sides and between said distal and proximal ends and said first and second side surfaces are each planar.

21. The device of 18, wherein said first and second side surfaces extend between said opposite sides and between said distal and proximal ends.

22. A tissue retraction device for surgery in a patient, comprising:
   a retractor comprising a first retractor portion and a second retractor portion, wherein each of said first and second retractor portions includes an elongated blade portion extending between a proximal end and a distal end, wherein said distal ends are positionable in the patient, each of said blade portions including a radiolucent portion extending between said distal and proximal ends and between opposite sides of said blade portion, each of said blade portions further including a radio-opaque longitudinal member extending on at least one of said opposite sides thereof in a direction between said distal and proximal ends to define at least a portion of a perimeter edge of said blade portion wherein said perimeter edge and said radio-opaque longitudinal member extend to opposite side surfaces of said elongated blade portion, said radio-opaque longitudinal member providing an indication of a location and extent of said blade portion in the patient, wherein said first and second retractor portions are positioned relative to one another so that said elongated blade portions form a working channel therebetween extending between said distal and proximal ends, each of said blade portions including a passage configured for receiving a surgical instrument, said passage extending between a first opening extending through the proximal end of the respective blade portion and a second opening extending through one of said opposite sides of the respective blade portion, said first opening being positioned equidistant between said opposite sides.

23. The device of claim 22, wherein said radio-opaque longitudinal member of each said retractor portions includes first and second radio-opaque longitudinal members extending on a respective one of said opposite sides of said respective blade portion to define opposite outer perimeter edges of said blade portion, wherein said first radio-opaque longitudinal members of said retractor portions are positioned adjacent one another and said second radio-opaque longitudinal members of said retractor portions are positioned adjacent one another when said first and second retractor portions are positioned to form said working channel.

24. The device of claim 23, wherein said blade portion of each of said first and second retractor portions includes an inner surface extending between said respective first and second longitudinal members thereof, said inner surfaces being oriented toward one another to form said working channel.

25. The device of claim 23, wherein said blade portions of each of said first and second retractor portions includes a radio-opaque transverse member extending from said first radio-opaque longitudinal member to said second radio-opaque longitudinal member along said distal end of said respective blade portion.

* * * * *